US008663148B2

(12) United States Patent
Larm et al.

(10) Patent No.: US 8,663,148 B2
(45) Date of Patent: Mar. 4, 2014

(54) DEVICE AND METHOD FOR RESTORATION OF THE CONDITION OF BLOOD

(75) Inventors: Olle Larm, Bromma (SE); Tomas Bergström, Gothenburg (SE); Jonas Axelsson, Stockholm (SE); Lars Adolfsson, Uppsala (SE); Robert S. Ward, Orinda, CA (US); Keith McCrea, Concord, CA (US)

(73) Assignee: Exthera Medical Corporation, Berkeley, CA (US)

( * ) Notice: Subject to any disclaimer, the term of this patent is extended or adjusted under 35 U.S.C. 154(b) by 806 days.

(21) Appl. No.: 12/665,156

(22) PCT Filed: Jun. 18, 2008

(86) PCT No.: PCT/US2008/067271
§ 371 (c)(1),
(2), (4) Date: Jun. 8, 2010

(87) PCT Pub. No.: WO2008/157570
PCT Pub. Date: Dec. 24, 2008

(65) Prior Publication Data
US 2010/0249689 A1 Sep. 30, 2010

(30) Foreign Application Priority Data
Jun. 18, 2007 (EP) .................................... 07110460

(51) Int. Cl.
*A61M 1/14* (2006.01)
*C08B 37/10* (2006.01)

(52) U.S. Cl.
USPC .......................................... 604/5.04; 536/21

(58) Field of Classification Search
USPC .......................................... 604/5.04; 536/21
See application file for complete search history.

(56) References Cited

U.S. PATENT DOCUMENTS

| 4,103,685 | A | | 8/1978 | Lupien et al. |
| 4,613,665 | A | * | 9/1986 | Larm .............................. 536/20 |
| 4,820,302 | A | * | 4/1989 | Woodroof ........................ 623/8 |
| 6,159,377 | A | | 12/2000 | Davankov et al. |
| 6,461,665 | B1 | * | 10/2002 | Scholander ................. 427/2.24 |
| 6,653,457 | B1 | * | 11/2003 | Larm et al. ..................... 536/20 |
| 2002/0197249 | A1 | | 12/2002 | Brady et al. |
| 2004/0202783 | A1 | | 10/2004 | Baumann et al. |
| 2009/0105194 | A1 | * | 4/2009 | Flengsrud et al. ............. 514/56 |
| 2009/0136586 | A1 | * | 5/2009 | Larm et al. ................... 424/529 |

FOREIGN PATENT DOCUMENTS

| DE | 42 17 917 A1 | 12/1993 |
| EP | 0 533 946 A1 | 3/1993 |
| JP | 96-510166A A | 10/1996 |
| JP | 2005-514127 A | 5/2005 |
| WO | WO-9426399 A1 | 11/1994 |
| WO | WO-97/35660 A1 | 10/1997 |
| WO | WO-2003057356 A2 | 7/2003 |
| WO | WO-2007/058592 A1 | 5/2007 |
| WO | WO-2007/069983 A1 | 6/2007 |

OTHER PUBLICATIONS

Fujita et al., "Adsorption of Inflammatory Cytokines Using a Heparin-Coated Extracorporeal Circuit", *Artificial Organs*, Blackwell Publishing, Inc., vol. 26, No. 12, 2002, pp. 1020-1025.
European Examination Report issued on May 6, 2010 in European Application No. 08 771 301.2.
English language translation of Office Action issued in corresponding Chinese Patent Application No. 200880025586.
Sanchez, J. et al., "Control of contact activation on end-point immobilized heparin: The role of antithrombin and the specific antithrombin-binding sequence," The Journal of Biomedical Materials Research, 1995, vol. 29, pp. 665-661.

* cited by examiner

*Primary Examiner* — Wu-Cheng Winston Shen
*Assistant Examiner* — Yih-Horng Shiao
(74) *Attorney, Agent, or Firm* — Birch, Stewart, Kolasch & Birch, LLP

(57) ABSTRACT

The present invention relates to a device for extracorporeal removal of harmful agents from blood or blood components, comprising full length heparin immobilized on a solid substrate by covalent end point attachment. The present invention also relates to a method for extracorporeal removal of a harmful agent from mammalian blood or blood components. The present invention further relates to a process for covalent end point attachment of full length heparin to a solid substrate.

32 Claims, No Drawings

DEVICE AND METHOD FOR RESTORATION OF THE CONDITION OF BLOOD

FIELD OF THE INVENTION

The present invention relates to a device for extracorporeal removal of harmful agents from blood or blood components, the device comprising full length heparin immobilized on a solid substrate by covalent end point attachment. The present invention also relates to a method for extracorporeal removal of a harmful agent from mammalian blood or blood components. The present invention further relates to a process for covalent end point attachment of full length heparin to a solid substrate.

BACKGROUND

Sepsis is most commonly induced by a systemic infection of Gram negative bacteria and today, when infections caused by antibiotic resistant strains of bacteria constitute a major problem, alternative methods for prevention and treatment are required. Earlier studies, in vitro and in vivo, have revealed that compositions containing immobilized heparin have prophylactic properties on microbial infections. Also, an inflammatory response caused by bioincompatibility of extracorporeal circuits is a major clinical issue and can ultimately lead to sepsis.

Heparan sulfates are proteoglycans that are present on the surface of almost all mammalian cells. Many microorganisms utilize heparan sulfates on the surface of the mammalian cell as receptors. Furthermore, inflammatory cells and cytokines utilize heparan sulfates on the cell surface for binding and activation. Heparin is another proteoglycan with a molecular weight of 15-25 kDa that is isolated from proteoglycans in basophilic granules of mast cells in mammalian tissue. Due to the structural similarity between heparin and heparan sulfates, heparin immobilized on a solid surface binds bacteria, virus and parasites as well as inflammatory cells and cytokines.

The development of a pro-inflammatory state is associated with a dramatically increased morbidity and mortality in a number of mammalian diseases, including septicemia, viraemia, acute or chronic renal disease, cardiovascular disease, hypovolemic shock, anaphylactic reactions and autoimmune disease. Tissue damage and organ dysfunction may be caused not only by alien microorganisms, but also by pro-inflammatory mediators released in response to such an infection or due to surface activation by conventional extracorporeal circuits (complement activation, etc.). Cytokines (such as tumor necrosis factor, interleukin-1, interleukin-6) and non-cytokines (such as nitric oxide, platelet-activating factor, complements, and eicosonoids) may inflict collateral tissue injury and contribute to the dysfunction of multiple organ systems as well as to organism cell death. Components from bacteria, parasites, fungi, or viruses may evoke the activation of pro-inflammatory cytokines through a plethora of cell-types. Inflammatory cells, including macrophages, lymphocytes, and granulocytes, are activated. Endogenous anti-inflammatory mediators are released in response to the infection and act to control the overwhelming systemic inflammatory response. First, the removal of pathogenic microorganisms is pivotal to diminish the inflammatory response. Second, the fragile balance between negative and positive feedback on the inflammatory mediators is the key factor that modulates the cellular damage and influences the clinical outcome, thus making the reduction of circulating pro-inflammatory stimuli and/or pro-inflammatory cytokines a key event in controlling septic complications.

U.S. Pat. No. 6,197,568 discloses methods for isolation, diagnosis and treatment of microorganisms such as flaviviruses and other hemorrhagic viruses based on the interaction of said microorganisms with heparin immobilized on agarose. Heparin-agarose as used in U.S. Pat. No. 6,197,568 comprises cleaved heparin molecules immobilized on agarose.

In *Artificial Organs*, 26(12):1020-1025 (2002) inflammatory cytokines are adsorbed using a heparin coated extracorporeal circuit. The extracorporeal circuit was provided with a Baxter Duraflo II heparin surface with electrostatically bound multi point attached heparin.

There is a demand for improved methods and devices for extracorporeal treatment of blood.

SUMMARY OF THE INVENTION

It is an object of the present invention to provide improved devices and methods for the extracorporeal removal of harmful agents from mammalian blood or blood components.

Another object of the present invention is to provide a device for removal of harmful agents from mammalian blood or blood components for use in conventional extracorporeal circulation systems for e.g. hemodialysis or oxygenation.

A further object of the present invention is to provide a method for immobilization of full length heparin onto the device without altering the wanted biological activities of the heparin molecules. Furthermore, the surface shall be stable under the reaction conditions used, especially with respect to leaching of heparin.

DETAILED DESCRIPTION OF THE INVENTION

In a first aspect thereof, the present invention provides a device for extracorporeal removal of harmful agents from blood or blood components, the device comprising hill length heparin immobilized on a solid substrate by covalent end point attachment.

The most successful technology for heparinization of surfaces currently in use is the Carmeda Bioactive Surface (CBAS®). In the preparation of CBAS® surfaces, the heparin molecules are cleaved order to provide reactive groups for end point attachment of the heparin fragments to surfaces. End point attachment of the polysaccharide is necessary to make it possible for heparin binding moieties to get access and bind to the heparin molecules. The mean molecular weight of the heparin molecules attached by the CBAS® procedure is 6-9 kDa.

In a device according to the present invention, a technology for heparin immobilization is used, wherein full length heparin molecules with a mean molecular weight of more than 21 KDa are end-point attached to surfaces. Using a process of the present invention, the amount of heparin attached to a surface can be almost doubled as compared to the present CBAS® state of the art. The longer chains attached by the method of the present invention also provides a spacer function that leads to a larger amount of accessible heparin oligomers available for heparin binding moieties to bind to.

The present inventors have found that a full length heparin coated surface according to the present invention binds TNF-α much more efficiently than a conventional surface coated with heparin fragments as generally employed in the prior art. In the prior art, most heparin coated surfaces have been prepared by methods that involve fragmentation of the heparin molecules in order to obtain reactive groups useful in coupling the heparin fragments to solid substrates. Previous attempts to couple full length heparin to solid surfaces have resulted in heparin surfaces with low surface concentrations of coupled heparin, not useful in practical applications. Other previous attempts to couple full length heparin to solid surfaces have resulted in multi-point attachment of the heparin molecules to the solid substrate, which greatly reduces the binding capacity of the heparin.

Thus, in an embodiment of the invention, the immobilized heparin molecules have a mean molecular weight of more than 10 kDa. In another embodiment of the invention, the immobilized heparin molecules have a mean molecular weight of more than 15 kDa. In yet another embodiment of the invention, the immobilized heparin molecules have a mean molecular weight of more than 21 kDa. In yet another embodiment of the invention, the immobilized heparin molecules have a mean molecular weight of more than 30 kDa. Preferably, the immobilized heparin molecules have a mean molecular weight within the range of 15-25 kDa. The mean molecular weight may also be higher, such as in the range of 25-35 kDa.

The mean molecular weight of the immobilized heparin molecules in a device according to the present invention is thus significantly higher than the mean molecular weight of the heparin molecules used in the current state of the art. The full length heparin molecules used in accordance with the present invention provide improved binding capacity for heparin binding moieties both in terms of the amount of heparin binding molecules that can be bound per surface area unit of the solid substrate, and in terms of the range of molecules that can be bound by the surface due to the increased selection of binding motifs presented by the immobilized full length heparin molecules.

The present invention relates to a process for the preparation of surfaces carrying end-point attached full length heparin, which method results in full length heparin coated surfaces having a high surface concentration of full length heparin. The full length heparin molecules used in the various aspects of the present invention provide a significant increase in the binding capacity for heparin binding entities per surface area unit as compared to the heparin surfaces of the prior art. The heparin is preferably covalently linked to said solid substrate. Covalent coupling of the heparin molecules prevent leaching of heparin into blood in contact with the heparin coated surface. Leaching of heparin has been a problem in prior art techniques employing for example electrostatic binding of heparin to surfaces.

In a more specific embodiment, said heparin is linked to said solid substrate by covalent end-point attachment. Covalent attachment of heparin to a solid substrate provides better control of parameters such as surface density and orientation of the immobilized molecules as compared to non-covalent attachment. The present inventors have found that these parameters are important in order to provide optimal binding of heparin binding harmful agents to the immobilized heparin molecules. In an embodiment, the surface concentration of the heparin on the solid substrate is in the range of 1-20 $\mu g/cm^2$. In another embodiment, the surface concentration of the heparin on the solid substrate is in the range of 5-15 $\mu g/cm^2$. Covalent end-point attachment means that the heparin is covalently attached to the solid substrate via the terminal residue of the heparin molecule.

In an embodiment of the invention, the covalent attachment of full length heparin molecules to a surface is achieved by the reaction of an aldehyde group of the heparin molecule with a primary amino group present on the surface. An inherent property of all carbohydrates is that they have a hemiacetal in their reducing end. This acetal is in equilibrium with the aldehyde form and can form Schiff's bases with primary amines. These Schiff's bases may then be reduced to stable secondary amines. In an embodiment of the inventive device, said heparin is covalently attached to said solid substrate via a stable secondary amino group.

In an embodiment, the device is a column comprising a casing containing the heparinized solid substrate, said column having an inlet through which blood may enter the column and an outlet through which blood may exit the column and said inlet and outlet are arranged such that blood entering through the inlet is brought into contact with said heparinized solid substrate before it exits the column through the outlet.

The solid substrate of the device may preferably comprise a material having a large surface area. The solid substrate of the device may comprise microparticles or hollow fibres, but other types of solid substrates may also be used. The total surface area of said solid substrate may be in the range of 0.1-20 $m^2$, preferably in the range of 0.5-3 $m^2$. In certain embodiments of the invention, the material of said solid substrate is selected from the group consisting of glass, cellulose, cellulose acetate, chitin, chitosan, crosslinked dextran, crosslinked agarose, cross linked alginate, polyethylene, polypropylene, polysulfone, polyacrylonitrile, silicone, fluoropolymers (such as polytetrafluoroethylene) and polyurethanes.

The solid substrate may comprise particles or beads. In an embodiment of the inventive device, wherein the solid substrate is particles or beads, said particles or beads may preferably comprise a material selected from the group consisting of polyurethanes, polyolefins, silicones, fluoropolymers (such as polytetrafluoroethylene), poly(methyl methacrylate), glass, cross linked alginates, and cross linked polysaccharides, such as agarose, dextran, cellulose, chitosan and starch. Other materials commonly used in microparticles for medical applications may also be employed. In another embodiment of the invention, the solid substrate comprises a cross linked polysaccharide.

In an embodiment of the inventive device, wherein the solid substrate comprises hollow fibers, said hollow fibers may preferably comprise a material selected from the group consisting of polysulfones, polyamides, polynitriles, polypropylenes, cross linked alginates, and cellulose. Other materials commonly used in hollow fibers for medical applications may also be employed. The hollow fiber may preferably comprise a polysulfone.

The solid substrate of the device may of course also be present in other shapes or forms providing a large surface area.

The size and porosity of the solid substrate should be selected for each application or treatment so as to allow a suitable blood flow rate through the device at an acceptable pressure drop over the device. For certain applications requiring a high blood flow rate and a low pressure drop, a larger diameter particle, pore, hollow fiber or other solid substrate is required. In other applications that do not require a high blood flow rate and a low pressure drop, smaller diameter particles, pores, hollow fibers or other solid substrates may be used. Thus, in an embodiment of the present invention, wherein the solid substrate is present in the form of particles, the particle diameter may be in the range of 10 $\mu m$ to 5 mm. The particle diameter may also be in the range of 10 $\mu m$ to 1000 $\mu m$. Generally, a particle size in the range of 20-200 $\mu m$ is useful, but in high flow rate applications larger particles may be required. The solid substrate may comprise one or more hollow fibers. In an embodiment of the present invention, wherein the solid substrate is present in the form of hollow fibers, the inner diameter of said fibers may be in the range of 1 μm to 1000 μm. Generally, an inner diameter in the range of 20-200 μm is useful, but in certain applications larger or smaller diameter fibers may be employed.

The device of the present invention should preferably be suitably dimensioned for the blood flow rate required in the application for which it is intended. As non limiting examples, the blood flow rate in extracorporeal circuits for renal dialysis is generally in the range of 200-500 mL/min, whereas the blood flow rate in extracorporeal circuits for oxygenation is generally in the range of 2000-7000 mL/min. In certain applications, such as in extracorporeal circuits for treatment of acute sepsis, the blood flow rate may be much lower, e.g. in the range of 1-100 mL/min.

Thus, in an embodiment, the device of the present invention is suitable for a blood flow of 200-500 mL/min. In another embodiment, the device of the present invention is suitable for a blood flow of 2000-7000 mL/min. In yet another embodiment, the device of the present invention is suitable for a blood flow of 1-100 mL/min.

Local blood flow patterns in blood contacting medical devices for extracorporeal circulation are known to influence clot formation via shear activation and aggregation of platelets in stagnant zones. Consequently, the device of the present invention should be designed in a fashion that does not create these problems.

In an embodiment, the inventive device is arranged in a venous-to-venous or arterial-to-venous extracorporeal bypass circuit. Such a circuit may further comprise a pump, tubing and cannulae. The device may preferably be suitable for the required blood flow for different medical procedures.

In another embodiment, the inventive device comprises a pump for transporting blood through the device. In a particular embodiment, the device may be presented as a stand-alone unit, which may be operated independently of other equipment.

In an embodiment of the first aspect of the invention, the device is a column arranged for use with an extracorporeal circuit. The column comprises a casing containing the heparinized solid substrate, said column having an inlet through which blood may enter the column and an outlet through which the blood may exit the column and said inlet and outlet are arranged such that blood entering through the inlet is brought in contact with said heparinized solid substrate before it exits the column through the outlet. The heparinized solid substrate is coated with covalently end-point attached full length heparin at a surface concentration of approximately 10 μg/cm².

A device according to the present invention may for example be useful in the treatment or prevention of indications such as septic shock, septicaemia, disseminated intravascular coagulation, autoimmune diseases, transplant rejection. Other clinical applications involve removal of micro organisms (e.g. malaria, hepatitis C and HIV) and heparin-binding poisons (e.g. snake venom). Use of the inventive device in combination with conventional circuits for extracorporeal circulation, including oxygenators and dialysis machines, will decrease morbidity and mortality associated with long term use of such circuits.

The harmful agents of the present invention may for example be pro-inflammatory mediators, such as pro-inflammatory cells or pro-inflammatory proteins. However, the device of the present invention is not limited to the removal of pro-inflammatory cells and pro-inflammatory proteins. Any endogenous or exogenous molecule having a binding affinity for heparin may be removed using the inventive device. Also microorganisms comprising a molecule having a binding affinity for heparin may be removed using the inventive device. Microorganisms and molecules that may be removed from blood using a device according to the present invention comprise for example microorganisms selected from the group consisting of bacteria, viruses and parasites, along with proteins or other molecules encoded by or associated with such microorganisms.

In an embodiment, said harmful agent is a virus. In a more specific embodiment, said virus is selected from the group consisting of herpes simplex virus type 1, herpes simplex virus type 2, Influenza A virus, cytomegalovirus and human immunodeficiency virus. In another more specific embodiment, said virus is selected from the group consisting of herpes simplex virus type 1 or herpes simplex virus type 2.

In another embodiment, said harmful agent is a bacterium. In a more specific embodiment, said bacterium is selected from the group consisting of streptococci, such as *Streptococcus pneumoniae*, staphylococci, such as *Staphylococcus aureus*, coli, such as *Escherichia coli*, pseudomonas, such as *Pseudomonas aureginosa*, and pneumococci, such as *Pneumococcus* type 2. In a preferred embodiment, said harmful agent is *Staphylococcus aureus*.

In yet another embodiment, said harmful agent is a parasite. In a more specific embodiment, said parasite is selected from the group consisting of *Plasmodium falciparum* and *Trypanosoma cruzi*.

In a further embodiment, the pro-inflammatory mediator may be an inflammatory cell selected from the group consisting of inflammatory lymphocytes, inflammatory macrophages and inflammatory granulocytes.

In yet a further embodiment, the pro-inflammatory mediator may be a pro-inflammatory protein, such as a pro-inflammatory cytokine. Examples of pro-inflammatory proteins include proteins containing heparin binding motifs as disclosed in *J. Biol. Chem.*, 2007, Mar. 30; 282(13):10018-27, and proteins selected from the group consisting of tumor necrosis factor, interleukin-1, interleukin-6, protein C, interleukin-8, high-mobility group box-1 protein or macrophage migratory inhibitory factor. In a more specific embodiment, said pro-inflammatory cytokine is selected from the group consisting of tumor necrosis factor alpha (TNF-α), tumor necrosis factor beta (TNF-β), interleukin-1 (IL-1), and interleukin-6 (IL-6).

In a second aspect thereof, the present invention provides a method for extracorporeal removal of a harmful agent from mammalian blood, comprising the steps:

a) providing a sample of mammalian blood,
b) bringing said sample into contact with full length heparin immobilized on a solid substrate by covalent end point attachment, under conditions allowing binding of said harmful agent to the heparin,
c) separating the sample from the solid substrate, such that said harmful agent is at least partially retained on the solid substrate, and
d) recovering said sample containing a reduced amount of said harmful agent.

In an embodiment of the second aspect of the present invention, step b) and c) of the method are performed using a device as defined by the first aspect of the invention. Further embodiments of a method according to the second aspect of the invention correspond to those specified above for the device according to the first aspect of the present invention regarding the harmful agent, inflammatory cell, inflammatory protein, mammalian blood, solid substrate and heparin immobilization.

In a third aspect thereof, the present invention provides a method for treatment of a mammalian subject suffering from a condition caused or aggravated by a harmful agent, comprising the steps:

a) extracting blood from the subject, b) bringing the extracted blood into contact with full length heparin immobilized on a solid substrate by covalent end point attachment, under conditions allowing binding of said harmful agent to the heparin, c) reintroducing the blood, containing a reduced amount of said harmful agent, into the bloodstream of the subject.

In an embodiment of the third aspect of the present invention, step b) of the method is performed using a device as defined by the first aspect of the invention. Further embodiments of a method according to the third aspect of the invention correspond to those specified above for the device according to the first aspect of the present invention regarding the harmful agent, inflammatory cell, inflammatory protein, mammalian blood, solid substrate and heparin immobilization.

In an embodiment, the methods of the invention may be used for removal of pro-inflammatory cytokines from mammalian blood.

In a fourth aspect thereof, the present invention provides an apparatus for extracorporeal circulation of blood or blood components, comprising a conventional extracorporeal blood treatment device and a device for removal of harmful agents as described herein.

Treatment of conditions such as sepsis or renal failure in a patient often involve treatment of the patient's blood in an extracorporeal circuit comprising a dialysis device. The treatment method used in extracorporeal blood treatment may itself induce activation of inflammatory cytokines resulting in an increase of these substances in the bloodstream of the patient under treatment. Activation of cytokines may for example be caused by mechanical stress imparted on the blood during transport through tubing, connections and components of an extracorporeal blood treatment system. Another example of where this is an important issue is in oxygenators used to oxygenate blood during for example acute pulmonary failure after trauma. In particular, the transport of blood through narrow diameter pores or channels may cause shear stress on the blood cells present in the blood. Also, the surface material of the different components with which the blood is brought in contact may affect the activation of inflammatory cytokines in the blood. An apparatus according to the present invention decreases the problems associated with activation of pro-inflammatory cytokines occurring in conventional blood treatment devices.

Embodiments of a method according to the fourth aspect of the invention correspond to those specified above for the method according to the first aspect of the present invention regarding the harmful agent, inflammatory cell, inflammatory protein and mammalian blood.

In an embodiment of the apparatus, said conventional extracorporeal blood treatment device is a device for oxygenation of blood.

In another embodiment of the apparatus, said conventional extracorporeal blood treatment device is a device for hemodialysis.

Other types of conventional extracorporeal blood treatment devices are also contemplated for use in the apparatus of the present invention.

In the apparatus of the invention, the device for removal of harmful agents should preferably be arranged downstream of the conventional extracorporeal blood treatment device.

In a preferred embodiment of the inventive apparatus, said device for removal of harmful agents comprises heparin immobilized on a solid substrate.

The solid substrate of the device for removal of harmful agents may preferably comprise a material having a large surface area. The solid substrate of the device may comprise microparticles or hollow fibres, but other types of solid substrates may also be used. The total surface area of said solid substrate may be in the range of 0.1-20 $m^2$, preferably in the range of 0.5-3 $m^2$.

The solid substrate may comprise particles or beads. In an embodiment of the apparatus, wherein the solid substrate is particles or beads, said particles or beads may preferably comprise a material selected from the group consisting of polyurethanes, polyolefins, silicones, fluoropolymers (such as polytetrafluoroethylene), poly(methyl methacrylate), glass, cross linked alginates, and cross linked polysaccharides, such as agarose, dextran, cellulose, chitosan and starch. Other materials commonly used in microparticles for medical applications may also be employed. In another embodiment, the solid substrate comprises a cross-linked polysaccharide.

In an embodiment of the apparatus, wherein the solid substrate comprises hollow fibers, said hollow fibers may preferably comprise a material selected from the group consisting of polysulfones, polyamides, polynitriles, polypropylenes, cross linked alginates, and cellulose. Other materials commonly used in hollow fibers for medical applications may also be employed.

The solid substrate of the apparatus may of course also be present in other shapes or forms providing a large surface area.

In an embodiment of the apparatus according to the present invention, wherein the solid substrate is present in the form of particles, the particle diameter may be in the range of 10 μm to 5 mm. The particle diameter may also be in the range of 10 μm to 1000 μm. Generally, a particle size in the range of 20-200 μm is useful, but in high flow rate applications larger particles may be required. The solid substrate may comprise one or more hollow fibers. In an embodiment, wherein the solid substrate is present in the form of hollow fibers, the inner diameter of said fibers may be in the range of 1 μm to 1000 μm. Generally, an inner diameter in the range of 20-200 μm is useful, but in certain applications larger or smaller diameter fibers may be employed.

The device for removal of harmful agents may preferably be a column comprising a casing containing the heparinized solid substrate, said column having an inlet through which blood may enter the column and an outlet through which blood may exit the column and said inlet and outlet are arranged such that blood entering through the inlet is brought into contact with said heparinized solid substrate before it exits the column through the outlet.

The apparatus of the present invention should preferably be suitably dimensioned for the blood flow rate required in the application for which it is intended. Thus, in an embodiment, the apparatus of the present invention is suitable for a blood flow of 200-500 mL/min. In another embodiment, the apparatus of the present invention is suitable for a blood flow of 2000-7000 mL/min. In yet another embodiment, the apparatus of the present invention is suitable for a blood flow of 1-100 mL/min. The device for removal of harmful agents should preferably be designed in a fashion that does not create clot formation via shear activation and aggregation of platelets in stagnant zones.

The surface concentration of said heparin may preferably be in the range of 1-20 μg/$cm^2$, preferably 5-15 μg/$cm^2$. The immobilized heparin of said device may preferably be covalently attached to the solid substrate. The immobilized heparin of said device is covalently attached to said solid substrate via stable secondary amino groups. More preferably, the immobilized heparin of said device is covalently end point attached full length heparin. Thus, in an embodiment of the apparatus according to the fourth aspect of the invention, the device for removal of harmful agents may be a device as disclosed above in reference to the first aspect of the invention.

In a fifth aspect thereof, the present invention provides use of an apparatus as defined above for extracorporeal treatment of blood or blood components.

In an embodiment, an apparatus as defined as defined above is used for treatment of a patient in need of hemodialysis. In such an embodiment the flow rate of said blood or blood component may preferably be in the range of 200-500 mL/min.

In another embodiment, an apparatus as defined above is used for treatment of a patient in need of oxygenation. In such an embodiment, the flow rate of said blood or blood component may preferably be in the range of 2000-7000 mL/min.

In yet another embodiment, an apparatus as defined above is used for treatment of a patient suffering from acute sepsis. In such an embodiment, the flow rate of said blood or blood component is in the range of 1-100 mL/min.

Further uses of an apparatus of the present invention will be apparent to a person skilled in art of extracorporeal treatment of blood.

In a further aspect of the invention a process for covalent end point attachment of full length heparin to a solid substrate is provided, said process comprising the steps of:
a) providing a solid substrate having primary amino functional groups,
b) mixing said solid substrate of a) with full length heparin and a reducing agent in an aqueous medium,
c) allowing the heparin to bind reductively to the amino functional groups, and
d) recovering the solid substrate having covalently bound full length heparin on its surface.

In an embodiment the initial concentration of full length heparin in the mixture is in the range of 20-50 g/l. The reducing agent used in the inventive process may be any suitable reducing agent as recognized by a person skilled in the art of organic synthesis. In an embodiment the reducing agent is $NaBH_3CN$. The reductive binding of step c) of the inventive process may preferably be performed at a pH-value in the range of 3-5. The reductive binding of step c) of the inventive process may preferably be performed at elevated temperature. In an embodiment, said reductive binding is performed at 60° C. for 24 h. The process may optionally comprise the additional step of a second addition of $NaBH_3CN$ during the reductive binding of step c).

As used herein the terms "blood" and "blood components" refer to mammalian whole blood, blood plasma and/or blood cells, such as for example red blood cells or platelets. It is also contemplated that the blood or blood components may be diluted or otherwise modified.

As used herein, the term "full length heparin" means heparin or derivatives thereof, which have not been cleaved in order to obtain reactive end groups for attachment to a solid surface. The molecular weight of full length heparin as present in vivo is generally distributed in the range of about 3-40 kDa. The molecular weight of heparin present in commercially available heparin preparations is generally distributed in the range of 15-25 kDa. The mean molecular weight of full length heparin is about 21 kDa.

As used herein, the term "harmful agent" may include a microorganism causative of diseases or disorders in mammals, such as a virus, a bacterium or a parasite, as well as harmful agents symptomatic of diseases or disorders, such as a pro-inflammatory cytokine. Examples of harmful microorganisms include *Staphylococcus*-species, HIV, hepatitis C, Dengue viruses and *Plasmodium* species causing malaria. The harmful agent may for example be a virus, such as herpes simplex virus type 1, herpes simplex virus type 2, Influenza A virus, cytomegalovirus or human immunodeficiency virus. The harmful agent may for example be a bacterium selected from the group consisting of streptococci, such as *Streptococcus pneumoniae*, staphylococci, such as *Staphylococcus aureus*, coli, such as *Escherichia coli*, pseudomonas, such as *Pseudomonas aureginosa*, and pneumococci, such as *Pneumococcus* type 2. The harmful agent may for example be a parasite such as *Plasmodium falciparum* or *Trypanosoma cruzi*. The harmful agent may for example be an inflammatory cell such as an inflammatory lymphocyte, an inflammatory macrophage or an inflammatory granulocyte. The harmful agent may also for example be inflammatory protein, such as a pro-inflammatory cytokine, for example tumor necrosis factor alpha (TNF-α), tumor necrosis factor beta (TNF-β), interleukin-1 (IL-1), and interleukin-6 (IL-6). The above mentioned examples of harmful agents should not be considered as limiting for the scope of the invention. As would be readily recognized by a person skilled in the art, all types of heparin binding harmful agents may be removed using a device or apparatus or method as disclosed by the present invention.

As used herein, the term "pro-inflammatory cell" means a cell, which is involved in inflammatory response in a mammal. Examples of "inflammatory cells" include inflammatory lymphocytes, inflammatory macrophages and inflammatory granulocytes.

As used herein, the term "pro-inflammatory protein" means a protein, such as a cytokine, released for instance in connection with microbial infection or immunization.

As used herein, the term "cytokine" means a protein, released for instance in connection with microbial infection or immunization, selected from the group consisting of interleukins, interferons, chemokines and tumour necrosis factors.

EXAMPLES

Example 1

General Method for Quantification of Surface Immobilized Heparin

The principle of this method is based on the chemical reaction between heparin and sodium nitrite in an acidic aqueous solution. The D-glucosamine units in heparin are converted into 2,5-anhydro D-mannose with simultaneous cleavage of the glycosidic linkage. The terminal aldehyde group in 2,5-anhydromannose reacts with 3-methyl-2-benzothiazolinone hydrazone hydrochloride hydrate (MBTH) to form a colored complex in the presence of iron (III) chloride-6-hydrate ($FeCl_3.6H_2O$). The color intensity of the complex is measured with a spectrophotometer at a wavelength of 650 nm.

Example 2

Amination of Sephadex G 10

Sodium metaperiodate ($NaIO_4$, 12.0 g) was dissolved in water (1.6 L) and added to Sephadex G 10 (100 g). The mixture was kept in the dark under shaking for 17 h. After filtration and washing with water (4 L) and finally with 0.1 M phosphate buffer (1 L), pH 7.0. The resulting product was suspended in a solution of 200 mL Lupasol® (5% in water) in 0.1 M phosphate buffer, pH 7.0 (1.2 L).

The gel was stabilized by addition of an aqueous solution of NaBH$_3$CN. Sodium cyanoborohydride (1.0 g) in 0.1 M phosphate buffer (200 mL), pH 7.0, was added to the gel mixture. The mixture was kept at room temperature under shaking for 24 h. The gel was filtered off and washed with water (2 L), 0.1 M phosphate buffer pH 7.0 (2 L), water (2 L), 0.1 M acetate buffer pH 4.0 (2 L) and water (2 L). The gel was air dried.

Example 3

Amination of Polyethylene Beads

Etching:

Polyethylene beads (PE beads) (diameter ca 300 μm, 60 g) were washed in chloroform (200 mL) during stirring for 1 hour. The beads were collected on a glass filter, washed with 3×50 mL of chloroform and left to dry in air. Potassium permanganate (KMnO$_4$, 1.2 g) was dissolved in concentrated sulfuric acid (600 mL) and the pre-washed beads were added. The suspension was stirred for 5 min. The beads were collected on a glass filter and carefully washed with water (5 L) and air dried.

Amination of Etched Beads:

The following solutions were prepared:

Aqueous borate buffer: Boric acid (53.0 g) and sodium chloride (3.5 g) were added to water (5.0 L). The pH value of the resulting solution was adjusted to 9.0 by the addition of sodium hydroxide pellets.

S1: To the aqueous borate buffer solution (5.0 L), crotonaldehyde (1.7 mL) and Lupasol® (5.0 mL, 5% aq) were added, resulting in the solution S1.

S2: Sodium chloride (146.5 g) and dextran sulfate (0.5 g) were added to water (5.0 L). The pH value of the resulting solution was adjusted to 3.0 by the addition of 1 M hydrochloric acid, resulting in the solution S2.

S3: Lupasol® (25 mL, 5% aq) was added to water (2.5 L) and pH was adjusted to 9.0 with 1 M NaOH, resulting in solution S3.

Coating Procedure:

1. The etched PE beads were added to S1 (2.5 L). The suspension was stirred for 10 min at room temperature.

2. The beads were collected on a glass filter and washed with water (2.5 L).

3. The beads were added to S2 (2.5 L). The suspension was stirred at 60° C. for 10 min.

4. The beads were collected on a glass filter and washed with water (2.5 L).

5. Step 1 was repeated with fresh S1.

6. The beads were collected on a glass filter and washed with water (2.5 L).

7. Step 2 was repeated with fresh S2.

8. The beads were collected on a glass filter and washed with water (2.5 L).

9. The resulting beads were added to S3 (2.5 L) and the suspension was stirred for 10 min at room temperature.

10. The beads were collected on a glass filter and washed with water (5.0 L), resulting in aminated PE beads.

Example 4

Covalent End-Point Attachment of Nitrous Acid Degraded Heparin onto an Aminated Chromatographic Gel Sephadex G 10 (10 g), aminated as described in Example 2, was suspended in 0.1 M acetate buffer pH 4.0 (100 mL) and nitrous acid degraded heparin (1.6 g) was added. After shaking for 15 min, NaBH$_3$CN (100 mg) dissolved in 0.1 M acetate buffer pH 4.0 (10 mL) was added. The reaction mixture was shaken for 24 h at room temperature and additional NaBH$_3$CN (100 mg) dissolved in 0.1 M acetate buffer pH 4.0 (10 mL) was added, and shaking was continued for another 24 h at room temperature.

The gel was filtered off and washed in turn with water (200 mL), 0.17 M borate buffer pH 9.0 (250 mL) and water (2 L). The gel was air dried.

Sephadex G10 beads have an average diameter of approximately 100 μm. A rough calculation reveals that 1 cm$^3$ contains $10^6$ beads which gives a surface area of 300 cm$^2$/cm$^3$. Sulfur analysis of the heparinazed Sephadex gel gave a result of 0.024% sulfur. Further, if heparin was attached only to the surface of the beads, the heparinized Sephadex G10 had approximately 7 μg heparin/cm$^2$.

Example 5

Covalent End-Point Attachment of Nitrous Acid Degraded Heparin onto an Aminated PE Beads Aminated PE beads, prepared as described in Example 3, were heparinized as described in Example 4.

By following the procedure described in Example 1, it was determined that the heparinized PE beads contained 2.6 mg heparin/g beads.

Example 6

Covalent End-Point Attachment of Full Length Heparin onto an Aminated Chromatographic Gel Sephadex G 10 (10 g), aminated as in Example 2, was suspended in 0.1 M acetate buffer, pH 4.0 (45 mL), and NaCl (1.46 g) and full length heparin (1.6 g) was added. After shaking for 0.5 h, NaBH$_3$CN (100 mg) dissolved in 0.1 M acetate buffer pH 4.0 (5 mL) was added. The reaction mixture was shaken for 24 h at 60° C. After 8 h, more NaBH$_3$CN (100 mg) was added. The gel was filtered off and washed in turn with water (200 mL), 0.17 M borate buffer pH 9.0 (250 mL) and water (2 L). The gel was air dried.

Sephadex G10 beads have an average diameter of approximately 100 μm. A rough calculation reveals that 1 cm$^3$ contains $10^6$ beads which gives a surface area of 300 cm$^2$/cm$^3$. Sulfur analysis of the heparinazed Sephadex gel gave a result of 0.037% sulfur. Further, if heparin was attached only to the surface of the beads, the heparinized Sephadex G10 had approximately 11 μg heparin/cm$^2$, i.e. approximately 36% more heparin was immobilized when using the full length heparin than when using the degraded heparin (c.f. Example 4)

Example 7

Covalent End-Point Attachment of Full Length Heparin onto Aminated PE Beads

Aminated PE beads, prepared as described in Example 3, were heparinized as described in Example 6.

By following the procedure described in Example 1, it was determined that the heparinized PE beads contained 2.6 mg heparin/g beads.

Example 8

Covalent End-Point Attachment of Nitrous Acid Degraded Heparin onto the Inner Lumen of Hollow Fibers In this example a pediatric haemoflow dialyzer is used. The fibers are made of polysulfone with an inner diameter of 200 microns and a wall thickness of 40 microns. The total surface area of the blood contacting material is 4000 cm$^2$ and the priming volume is 28 mL.

The amination procedure is performed as described in Example 3 for PE beads, with the exception that the etching step is omitted. Polysulfone is hydrophilic and does not need etching. Immobilization of heparin is performed essentially as described in Example 4, by pumping a solution containing nitrous acid degraded heparin together with NaBH$_3$CN into the fibers.

Because measurement of the amount of heparin is a destructive procedure, a reference dialyzer that has been heparinized under identical conditions is sacrificed and its fibers are subjected to sulfur analysis. The results reveal a heparin content of approx. 5 µg heparin/cm$^2$, which corresponds to a content of 20 mg heparin in the device.

Example 9

Covalent End-Point Attachment of Full Length Heparin onto the Inner Lumen of Hollow Fibers The experiment is performed as described in Example 8, with the exception that full length heparin is used. The results reveal a heparin content of approx. 8 µg heparin/cm$^2$, which corresponds to a content of 32 mg heparin in the device.

Example 10

Adherence of Tumor Necrosis Factor Alpha (TNF-α) in Plasma to Heparinized PE Beads Heparinized PE beads having nitrous acid degraded heparin (prepared as described in Example 5) or full length heparin (prepared as described in Example 7), were used. 200 mg beads were added to columns (1 mL) with a bayonet joint lid (MoBiTec, M1002).

Samples (0.5 mL) were withdrawn with a syringe from 4 mL plasma taken from a human patient. The plasma samples were passed through the respective columns during 30 seconds. TNF-α content in the samples before and after passage through columns was measured with a Quantikine® human TNF-α/TNFSF1A high sensitivity ELISA kit (R&D Systems) with an EVOLIS instrument (BioRad).

After passage through the column with 200 mg PE beads having nitrous acid degraded heparin, the remaining TNF-α concentration in the sample was 4.5 pg/ml. After passage through the column with 200 mg PE beads having full length heparin, the remaining TNF-α concentration in the sample was 4.1 pg/ml. Thus, the decrease in TNF-α concentration in plasma that has passed over 200 mg beads that are heparinized with full length heparin (Mw 20 kDa) is greater than the decrease with beads that are heparinized with nitrous acid degraded heparin (Mw 8 KDa).

Example 11

Adherence of Antithrombin (AT) to Heparinized PE Beads

Heparinized PE beads having nitrous acid degraded heparin (prepared as described in Example 5) or full length heparin (prepared as described in Example 7), were used. 200 mg beads were added to columns (2.5 mL) with a bayonet joint lid (MoBiTec, S1012).

Solutions of human antithrombin III (Octapharma), 2 IU/ml in tris buffer (pH 7.4), were added to the columns. After incubation for 15 minutes, antithrombin that had bound to low affinity sites on immobilized heparin was removed by washing with tris buffer several times. Then, antithrombin that had bound to high affinity sites on immobilized heparin was eluted using large volumes of 1 mg/ml heparin in tris buffer. The content of heparin-antithrombin complexes in the resulting eluate was determined in a Sysmex CA 1500 instrument (Sysmex) using the Berichrom Antithrombin III reagent (Sysmex). The results are shown in Table 1.

TABLE 1

| Amount of antithrombin bound to heparin | | |
|---|---|---|
| | MBTH assay (Example 1) | Antithrombin |
| Full length heparin | 2.6 mg heparin/g beads | 2.48 IU/g beads |
| Nitrous acid degraded heparin | 2.6 mg heparin/g beads | 1.65 IU/g beads |

From these results, it is clear that full length heparin binds 1.5 times more antithrombin per weight unit than nitrous degraded heparin does.

The invention claimed is:

1. A device for extracorporeal removal of a harmful agent having a binding affinity to heparin from blood or blood components, the device comprising a full length heparin immobilized on a solid substrate by a covalent end point attachment, where said covalent end point attachment is formed by a process comprising the steps of:
   a) providing said solid substrate having primary amino functional groups,
   b) mixing said solid substrate of a) with said full length heparin and a reducing agent in an aqueous medium,
   c) allowing said full length heparin to bind covalently to the amino functional groups, wherein the covalent binding reaction between said full length heparin and the amino groups is performed at 60° C., and
   d) recovering the solid substrate having said full length heparin covalently bound on its surface.

2. The device according to claim 1, wherein said full length heparin has a mean molecular weight in the range of 15-25 kDa.

3. The device according to claim 1, wherein said full length heparin has a mean molecular weight of more than 21 kDa.

4. The device according to claim 1, wherein the a surface concentration of said full length heparin is 1-20 µg/cm$^2$.

5. The device according to claim 1, wherein a surface concentration of said full length heparin is 5-15 µg/cm$^2$.

6. The device according to claim 1, wherein said full length heparin is covalently attached to said solid substrate via stable secondary amino groups.

7. The device according to claim 1, wherein a total surface area of said solid substrate is in the range of 0.5-3 m².

8. The device according to claim 1, wherein said solid substrate comprises a particle or a bead.

9. The device according to claim 8, wherein a diameter of the particle or the bead is in the range of 10-1,000 µm.

10. The device according to claim 9, wherein the diameter of the particle or the bead is in the range of 20-200 µm.

11. The device according to claim 8, wherein said particle or said bead comprises a material selected from the group consisting of polyurethanes, polyolefins, silicones, fluoropolymers, poly(methyl methacrylate), glass, cross linked alginates, and cross linked polysaccharides, wherein the cross linked polysaccharide are selected from the group consisting of agarose, dextran, cellulose, chitosan and starch.

12. The device according to claim 1, wherein said solid substrate comprises one or more hollow fibers.

13. The device according to claim 12, wherein an inner diameter of said hollow fiber is in the range of 10-1,000 µm.

14. The device according to claim 13, wherein the inner diameter of said hollow fiber is in the range of 20-200 µm.

15. The device according to claim 12, wherein said hollow fiber comprises a material selected from the group consisting of polysulfones, polyamides, polynitriles, polypropylenes, cross linked alginates, and cellulose.

16. The device according to claim 1, wherein the device is a column comprising a casing containing the full length heparin immobilized on the solid substrate, said column having an inlet through which blood enters the column and an outlet through which blood exits the column and said inlet and outlet are arranged such that blood entering through the inlet is brought into contact with said heparinized solid substrate before it exits the column through the outlet.

17. The device according to claim 16, suitable for a blood flow rate of 2,000-7,000 mL/min.

18. The device according to claim 16, suitable for a blood flow rate of 200-500 mL/min.

19. The device according to claim 16, suitable for a blood flow rate of 1-100 mL/min.

20. A method for extracorporeal removal of a harmful agent having a binding affinity to heparin from mammalian blood, comprising the steps:
    a) providing a sample of mammalian blood,
    b) bringing said sample into contact with the device of claim 1, under conditions allowing binding of said harmful agent to the heparin,
    c) separating the sample from the solid substrate, such that said harmful agent is at least partially retained on the solid substrate, and
    d) recovering said sample containing a reduced amount of said harmful agent.

21. The method according to claim 20, wherein said harmful agent is a pro-inflammatory cytokine.

22. A method for treatment of a mammalian subject suffering from a condition caused or aggravated by a harmful agent having a binding affinity to heparin, comprising the steps:
    a) extracting blood from the subject,
    b) bringing the extracted blood into contact with the device of claim 1, under conditions allowing binding of said harmful agent to the heparin,
    c) reintroducing the blood, containing a reduced amount of said harmful agent, into the bloodstream of the subject.

23. An apparatus for extracorporeal circulation of blood or blood components, comprising a second extracorporeal blood treatment device in addition to the device of claim 1.

24. The apparatus according to claim 23, wherein said device of claim 1 is arranged downstream of the second extracorporeal blood treatment device.

25. The apparatus according to claim 23, wherein a surface concentration of said heparin of the device of claim 1 is 1-20 µg/cm².

26. The apparatus according to claim 23, wherein said second extracorporeal blood treatment device is a device for hemodialysis.

27. The apparatus according to claim 23, wherein said second extracorporeal blood treatment device is a device for oxygenation of blood.

28. A process for forming a covalent end point attachment of a full length heparin to a solid substrate comprising the steps of:
    a) providing a solid substrate having primary amino functional groups,
    b) mixing said solid substrate of a) with said full length heparin and a reducing agent in an aqueous medium,
    c) allowing said full length heparin to bind covalently to the amino functional groups, wherein the covalent binding reaction between said full length heparin and the amino groups is performed at 60° C., and
    d) recovering the solid substrate having said full length heparin covalently bound on its surface.

29. The process according to claim 28, wherein a concentration of said full length heparin is in the range of 20-50 g/L.

30. The process according to claim 28, wherein the reducing agent is $NaBH_3CN$.

31. The process according to claim 28, wherein a pH-value of the aqueous medium of step b) is in the range of 3-5.

32. The process according to claim 28, further comprising a step of a second addition of $NaBH_3CN$ during the covalent binding of step c).

* * * * *